US010624386B2

(12) United States Patent
White (10) Patent No.: US 10,624,386 B2
(45) Date of Patent: *Apr. 21, 2020

(54) PELLET SUBSTRATES FOR VAPORIZING AND DELIVERING AN AEROSOL

(71) Applicant: Jackie L. White, Pfafftown, NC (US)

(72) Inventor: Jackie L. White, Pfafftown, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,534

(22) Filed: May 20, 2019

(65) Prior Publication Data
US 2019/0269170 A1 Sep. 5, 2019

Related U.S. Application Data

(63) Continuation-in-part of application No. 15/653,398, filed on Jul. 18, 2017, now Pat. No. 10,292,431.

(51) Int. Cl.
*A24B 15/16* (2020.01)
*A24B 15/167* (2020.01)
(Continued)

(52) U.S. Cl.
CPC .......... *A24B 15/165* (2013.01); *A24B 15/167* (2016.11); *A24B 15/283* (2013.01); *A24F 47/008* (2013.01); *A61M 11/003* (2014.02); *A61M 11/042* (2014.02); *A61M 11/048* (2014.02); *A61M 16/14* (2013.01); *A61M 2202/064* (2013.01);
(Continued)

(58) Field of Classification Search
None
See application file for complete search history.

(56) References Cited

U.S. PATENT DOCUMENTS 4,062,368 A * 12/1977 Crellin .................. A24D 3/163
131/332
4,596,259 A 6/1986 White et al.
(Continued)

OTHER PUBLICATIONS

European Patent Office (EPO), Patent Cooperation Treaty (PCT) International Search Report (ISR), dated Oct. 16, 2018 (Oct. 16, 2018), 6 pages, Rijswijk, Netherlands (NL), issued in International Application No. PCT/US2018/042194 filed Jul. 14, 2018 (Jul. 14, 2018).
(Continued)

*Primary Examiner* — Eric Yaary
(74) *Attorney, Agent, or Firm* — Christopher C. Dremann, P.C.; Christopher C. Dremann (57) ABSTRACT

Pellet substrates configured for use with a vapor delivery device to vaporize and deliver an aerosol to a user include a semi-porous base material formed of activated alumina pellets, activated carbon pellets, hulled millet grains that have a generally rounded shape or cellulose paper that has a generally disc shape. The pellet substrates are formed by mixing the base material with a liquid solution of an aerosol former and at least one of a tobacco extract mixture and a tobacco powder blend until the liquid solution is absorbed onto the exposed surfaces of the base material with or without drying by applying heat. The base material may be coated with a liquid hydrocolloid gum solution, namely a water soluble gum, such as sodium carboxymethyl cellulose, and distilled water to reduce fracturing, cracking, chipping and dusting of the pellet substrates.

16 Claims, 2 Drawing Sheets

(51) Int. Cl.
*A24F 47/00* (2020.01)
*A61M 11/00* (2006.01)
*A61M 11/04* (2006.01)
*A61M 16/14* (2006.01)
*A24B 15/28* (2006.01)

(52) U.S. Cl.
CPC ............... *A61M 2205/3368* (2013.01); *A61M 2205/3653* (2013.01); *A61M 2205/8206* (2013.01)

(56) References Cited

U.S. PATENT DOCUMENTS

| | | | |
|---|---|---|---|
| 4,714,082 | A | 12/1987 | Banerjee et al. |
| 4,756,318 | A | 7/1988 | Clearman et al. |
| 4,771,795 | A | 9/1988 | White et al. |
| 4,819,665 | A | 4/1989 | Roberts et al. |
| 4,827,950 | A | 5/1989 | Banerjee et al. |
| 4,836,225 | A | 6/1989 | Sudoh |
| 4,893,639 | A | 1/1990 | White |
| 4,913,169 | A | 4/1990 | Templeton |
| 4,989,619 | A | 2/1991 | Clearman |
| 5,020,548 | A | 6/1991 | Farrier et al. |
| 5,137,034 | A | 8/1992 | Perfetti et al. |
| 5,144,962 | A | 9/1992 | Counts et al. |
| 5,388,573 | A | 2/1995 | Mulhauser et al. |
| 5,388,574 | A | 2/1995 | Ingebrethsen |
| 5,396,911 | A | 3/1995 | Casey, III et al. |
| 5,460,173 | A | 10/1995 | Mulhauser et al. |
| 6,164,287 | A | 12/2000 | White |
| 8,251,060 | B2 | 8/2012 | White et al. |
| 8,915,254 | B2 | 12/2014 | Monsees et al. |
| 8,925,555 | B2 | 1/2015 | Monsees et al. |
| 9,016,274 | B1 | 4/2015 | White |
| 9,149,072 | B2 | 10/2015 | Conner et al. |
| 9,439,453 | B2 | 9/2016 | Conner et al. |
| 2004/0099269 | A1 | 5/2004 | Hale et al. |
| 2005/0013862 | A1 | 1/2005 | Tobyn et al. |
| 2006/0157491 | A1 | 6/2006 | Whittle et al. |
| 2008/0110470 | A1 | 5/2008 | Zhuang et al. |
| 2009/0275669 | A1 | 11/2009 | Aida et al. |
| 2011/0232657 | A1* | 9/2011 | Karles ............... A24B 15/186 131/275 |
| 2012/0067360 | A1 | 3/2012 | Conner et al. |
| 2013/0228170 | A1 | 9/2013 | Alper |
| 2013/0255702 | A1 | 10/2013 | Griffith, Jr. et al. |
| 2014/0261486 | A1* | 9/2014 | Potter ............... A24F 47/008 131/328 |
| 2015/0101606 | A1 | 4/2015 | White |
| 2015/0209530 | A1 | 6/2015 | White |
| 2015/0335070 | A1 | 11/2015 | Sears et al. |
| 2015/0359259 | A1 | 12/2015 | Conner et al. |
| 2016/0073695 | A1* | 3/2016 | Sears ............... H05B 3/46 131/329 |
| 2016/0219926 | A1 | 8/2016 | Whiffen |
| 2016/0295914 | A1 | 10/2016 | Jordil et al. |
| 2018/0014576 | A1 | 1/2018 | White |

OTHER PUBLICATIONS

European Patent Office (EPO), Patent Cooperation Treaty (PCT) Written Opinion of the International Searching Authority (ISA/WO), dated Oct. 16, 2018 (Oct. 16, 2018), 6 pages, Rijswijk, Netherlands (NL), issued in International Application No. PCT/US2018/042194 filed Jul. 14, 2018 (Jul. 14, 2018).

* cited by examiner

PELLET SUBSTRATES FOR VAPORIZING AND DELIVERING AN AEROSOL

CROSS-REFERENCE TO RELATED APPLICATION

This United States non-provisional utility patent application is a continuation-in-part of U.S. application Ser. No. 15/653,398 filed on Jul. 18, 2017, the entire disclosure of which is incorporated herein by reference.

FIELD OF THE INVENTION

The present invention relates to substrates useful for vaporizing and delivering an aerosol to a user. In exemplary embodiments, the invention is a substrate in the form of a pellet for use with a device operable to vaporize and deliver an aerosol to a user. In exemplary embodiments, the invention is a semi-porous, inert substrate in the form of a pellet that is adsorbed with an aerosol former and flavoring, nicotine, finely-ground tobacco powder, and/or tobacco extract for use with a heat-not-burn (HNB) device, such as a vaporizer, commonly referred to as a "vaping device" or a "vape device," to deliver a combustion-free aerosol to a smoker.

BACKGROUND OF THE INVENTION

The adverse health risks associated with smoking cigarettes are well known. It is estimated that at least seventy percent (70%) of smokers today desire to reduce the number of cigarettes they smoke, or to quit smoking altogether. Despite the known risks, only about six percent (6%) of smokers report that they were able to quit smoking entirely. The low rate of success is believed to be due to the highly addictive nature of the nicotine present in the tobacco of conventional cigarettes. Nicotine gum and nicotine patches are available for the delivery of nicotine without the harmful carcinogenic by-products of tobacco combustion. Nicotine gum and nicotine patches, however, have proven to be less successful as means for smoking cessation due to their failure to satisfy the hand-to-mouth and inhalation urges of a habitual smoker. In the past few years, nicotine delivery devices in the form of electronic cigarettes, also referred to as "smokeless cigarettes," "e-cigarettes." and "digital vapor cigarettes," as well as vape pens and vaporizers have been developed and introduced to the public. These devices operate combustion-free on the heat-not-burn (HNB) principle, and therefore, are believed to potentially eliminate the harmful carcinogenic by-products of tobacco combustion.

Popular brands of electronic cigarettes include BLU ECIGS® offered by Lorillard Technologies, Inc. of Greensboro, N.C., USA, VUSE® offered by Reynolds Innovations, Inc. of Winston-Salem, N.C., USA, MARK 1O™ offered by Phillip Morris, Inc. of Richmond, Va., USA, and NJOY® offered by NJOY, Inc. of Scottsdale, Ariz., USA. Popular brands of vape pens and vaporizers (collectively "vaporizers") include FIREFLY® offered by Firefly Company of San Francisco, Calif., USA, Matrix offered by Mig Vapor of Pompano Beach, Fla., USA, PAX® offered by PAX Labs, Inc. of San Francisco, Calif., USA, V2Pro offered by VMR Products, LLC of Miami, Fla., USA, HAZE® V3 offered by Haze Industries, Inc. of Atlanta Ga., USA, Ploom™ and Ploom TECH™ offered by Japan Tobacco Inc. of Tokyo, Japan, and the Iolite® WISPR® offered by Ogelsby & Butler of Carlow, Ireland.

Each of the aforementioned commercially available electronic cigarettes and vaporizers replicates the hand-to-mouth and inhalation experiences of a traditional tobacco cigarette desired by smokers. Electronic cigarettes and vaporizers can also satisfy a smoker's craving for addictive nicotine without exposing the smoker to the carcinogenic by-products produced by the combustion of tobacco, and without exposing by-standers to harmful second-hand smoke. As a result, electronic cigarettes and vaporizers are credited with providing a healthier nicotine delivery option to smokers, as well as a healthy environment for by-standers, by at least significantly reducing, and potentially eliminating, the harmful effects of the carcinogens present in the tobacco smoke that would otherwise be produced and dispersed by the combustion of tobacco with a conventional tobacco cigarette.

Conventional tobacco cigarettes are made of a combustible material that is ignited with a flame to cause the tobacco to burn. Burning tobacco releases a tobacco smoke containing nicotine that is inhaled by the smoker to deliver the nicotine to the lungs. Electronic cigarettes, on the other hand, heat a liquid, commonly referred to as "e-liquid," containing an aerosol former, such as glycerin, vegetable glycerin and/or propylene glycol, admixed with a flavoring and/or nicotine. The heat causes the e-liquid to produce an aerosol, commonly referred to as a "vapor" or "vape," that is inhaled by the smoker to deliver the flavoring and/or nicotine to the lungs. Most of the current electronic cigarettes include a battery energy source, an atomizer and a hollow, re-fillable or expendable cartridge that contains the e-liquid. Due to the frequency required to re-fill or replace the cartridge, an advanced type of electronic cigarette has been developed that combines the atomizer and the e-liquid cartridge into a single "cartomizer" electrically connected to the battery that allows for a greater period of time between re-fill and replacement.

The vaporization process is initiated by the smoker inhaling on a mouthpiece, or alternatively, by the smoker depressing a manual switch that activates the atomizer or cartomizer. The atomizer heats the e-liquid to cause the aerosol former to produce an inhalable aerosol containing the flavoring and/or nicotine. The aerosol is inhaled through the mouthpiece of the device to deliver the flavoring and/or nicotine to the lungs of the smoker. The smoker then exhales the residual aerosol vapor absent the harmful carcinogenic by-products of tobacco combustion. Vaporizers operate similarly to electronic cigarettes with the exception that most vaporizers utilize dry tobacco material as the substrate to be heated to release the aerosol containing nicotine that is vaporized and delivered to the smoker. Vaporizers are also commonly used with other dry plant (e.g., herb) material as the substrate, for example coffee, tea and marijuana.

Despite the reduced health risks, there remain certain disadvantages with the electronic cigarette devices that are currently available. For example, the e-liquid typically contains a volatile solution of propylene glycol, vegetable glycerin (VG), glycerin and/or polyethylene glycol 400 (PEG400) admixed with concentrated flavoring and/or a highly variable concentration of nicotine. Certain e-liquid solutions have been found to still contain known cancer-causing agents, referred to as tobacco-specific nitrosamines (TSNAs), as well as tobacco-specific impurities, such as anabasine, myosmine, and -nicotine. In fact, a recent study by the Food and Drug Administration (FDA) detected diethylene glycol, a poisonous and hygroscopic liquid commonly used in anti-freeze solutions, in a commercial e-liquid and a measurable level of nicotine in another commercial e-liquid that claimed to be nicotine-free.

These findings are particularly disturbing since the cartridges and cartomizers of electronic cigarettes that contain the e-liquid are inherently susceptible to leakage and/or breakage as a result of their small size and relative fragility. As a result, there exists a danger that a cartridge or cartomizer could leak or break, and thereby cause a user to directly inhale a harmful dosage of the e-liquid solution prior to vaporization. It is also possible for the e-liquid solution leaking from the cartridge or cartomizer to damage the electronics and/or corrode the battery of the vaporizer. Furthermore, the glycerin and/or propylene glycol aerosol former in the e-liquid is combustible, and thus, could ignite and cause a fire if the e-liquid solution comes into contact with an ignition source.

Certain disadvantages likewise exist with the vaporizers that are currently available. As previously mentioned, vaporizers typically utilize a dry plant material as the substrate that is heated to form the vapor to be delivered to the user in the form of an aerosol. The dry plant material is placed into a combination heating and aerosolizing (vaporizing) chamber, commonly referred to as the "oven." For the best results, it is essential that the dry plant material is finely ground and contains very little moisture, preferably less than about fifteen percent (15%). Accordingly, additional equipment, namely a fine particle grinder and a dryer are needed for optimal vaping. Furthermore, vaporizers that operate on the principle of conduction heating produce better vapor when a finely ground dry plant material is more tightly packed into the oven. Conversely, vaporizers that operate on the principle of convection heating produce better vapor when the unground dry plant material is more loosely packed into the oven. Regardless, the processes of grinding, drying and/or packing the dry plant material into the oven of the vaporizer, as well as subsequently removing the dry plant material residue and cleaning the oven, can be difficult, time consuming and variable, thereby making a consistently enjoyable vaping experience less likely.

Accordingly, an improved substrate for use with a vapor delivery device configured for vaporizing and delivering an aerosol to a patient or a smoker is needed. Furthermore, a substrate for vaporizing and delivering an aerosol is needed that is safe, relatively easy and convenient to use. In particular, a substrate for vaporizing and delivering an aerosol containing aerosol former and flavoring, nicotine, finely-ground tobacco powder and/or tobacco extract is desired that overcomes the problems, deficiencies and disadvantages of the electronic cigarettes and vaporizers that are currently available. Specifically, a semi-porous, inert substrate for vaporizing and delivering an aerosol to a smoker is needed that potentially eliminates the known risks of producing harmful carcinogenic by-products, inhaling an e-liquid solution, damaging a battery or electronics of the vapor delivery device or potentially causing a fire in the event of an e-liquid leak. Such a substrate should also not require the use of additional equipment or excessive time to prepare the substrate in the vapor delivery device or to subsequently clean the vapor delivery device, such that a consistently enjoyable vaping experience is obtained.

As used herein, the term "aerosol" means a colloidal system of solid and/or liquid particles dispersed and suspended in a gas, such as smoke or fog. The term "aerosol" is intended to include vapors, gases, fine particle suspensions, and the like, both visible and invisible. As so defined, the term "aerosol" specifically includes any pharmacologically or physiologically active agents and any desired additive, such as an aerosol former, flavoring, nicotine and/or an extract, irrespective of whether the mixture produces a visible aerosol. In exemplary embodiments of the invention shown and described herein, the aerosol is generated by a heat source acting upon a substrate adsorbed with an aerosol former. In specific exemplary embodiments, the aerosol former is admixed with flavoring, nicotine, finely-ground tobacco powder and/or tobacco extract in a manner consistent with the invention. As used herein, the term "in heat-conducting relation" is intended to mean an arrangement whereby heat is transferred by conduction or convection to a thermally conductive component, such as a heat conductor or a substrate, from a heat generating source, such as a heating element. A heat-conducting relation can be achieved by locating the thermally conductive component in direct physical contact or in sufficiently close proximity to the heat generating source, or alternatively, merely in fluid (e.g., air) communication with the heat generating source.

BRIEF DESCRIPTION OF THE DRAWING FIGURES

These and other features, aspects and advantages of the invention are better understood and appreciated when considered in light of the following detailed description of the invention with reference to the accompanying drawings.

DETAILED DESCRIPTION OF EXEMPLARY EMBODIMENTS OF THE INVENTION

The invention will be described more fully hereinafter with reference to the accompanying drawing figures in which various exemplary embodiments are shown. However, it is to be understood that the invention may be embodied in numerous different forms and should not be construed as limited to the exemplary embodiments set forth herein. Exemplary embodiments of the invention are provided herein so that this disclosure will both completely and accurately convey the scope of the invention, as well as enable one of ordinary skill in the art to make, use and practice the invention without undue experimentation. Like reference characters in the written description and accompanying drawing figures refer to the same or similar parts, elements, assemblies, subassemblies, systems and the like of the invention.

The exemplary embodiments provided herein show and describe pellet substrates for vaporizing and delivering an aerosol to a user. By way of example and not limitation, pellet substrates according to the invention are usable with a vapor delivery device to vaporize and deliver an aerosol containing a therapeutic drug to a patient, or similarly, an aerosol containing flavoring, nicotine and/or an extract to a smoker. As used herein, the term "aerosol" is intended to include vapors, gases, fine suspended particles, and the like, both visible and invisible. As so defined, "aerosol" specifically includes any pharmacologically or physiologically active agents and any desired additives, such as an aerosol former, flavoring, nicotine and/or an extract, irrespective of whether they produce a visible aerosol. Ideally, the aerosol has a density consistent with cigarette smoke and a small particle size on the order of about 0.2-3.0 microns. As used herein, the term "aerosol drug" refers to a therapeutic drug in the form of an aerosol available for delivery to a patient for use in inhalation therapy. Similarly, the term "aerosol nicotine" refers to flavoring, nicotine and/or an extract in the form of an aerosol available for delivery to a smoker via a vapor delivery device, and in particular, a combustion-free heat-not-burn (HNB) vapor device.

The aerosol, and more specifically the aerosol drug or the aerosol nicotine, is preferably produced by an aerosol former that is activated from heat generated by a heating element and/or conducted by a heat conductor. In certain instances, the heating element and/or the heat conductor may be one and the same component. A vapor delivery device suitable for use with pellet substrates for vaporizing and delivering an aerosol according to the invention provides a portable, effective, convenient, safe and simple to use means for reliably and repeatedly vaporizing and delivering a wide variety of pharmacologically or physiologically active agents to a user in the form of an aerosol. Such vapor delivery devices are particularly well suited and useful for vaporizing and delivering a therapeutic drug in the form of an aerosol drug to a patient, or alternatively, flavoring, nicotine and/or an extract in the form of aerosol nicotine to a smoker.

Figures 1, 2:
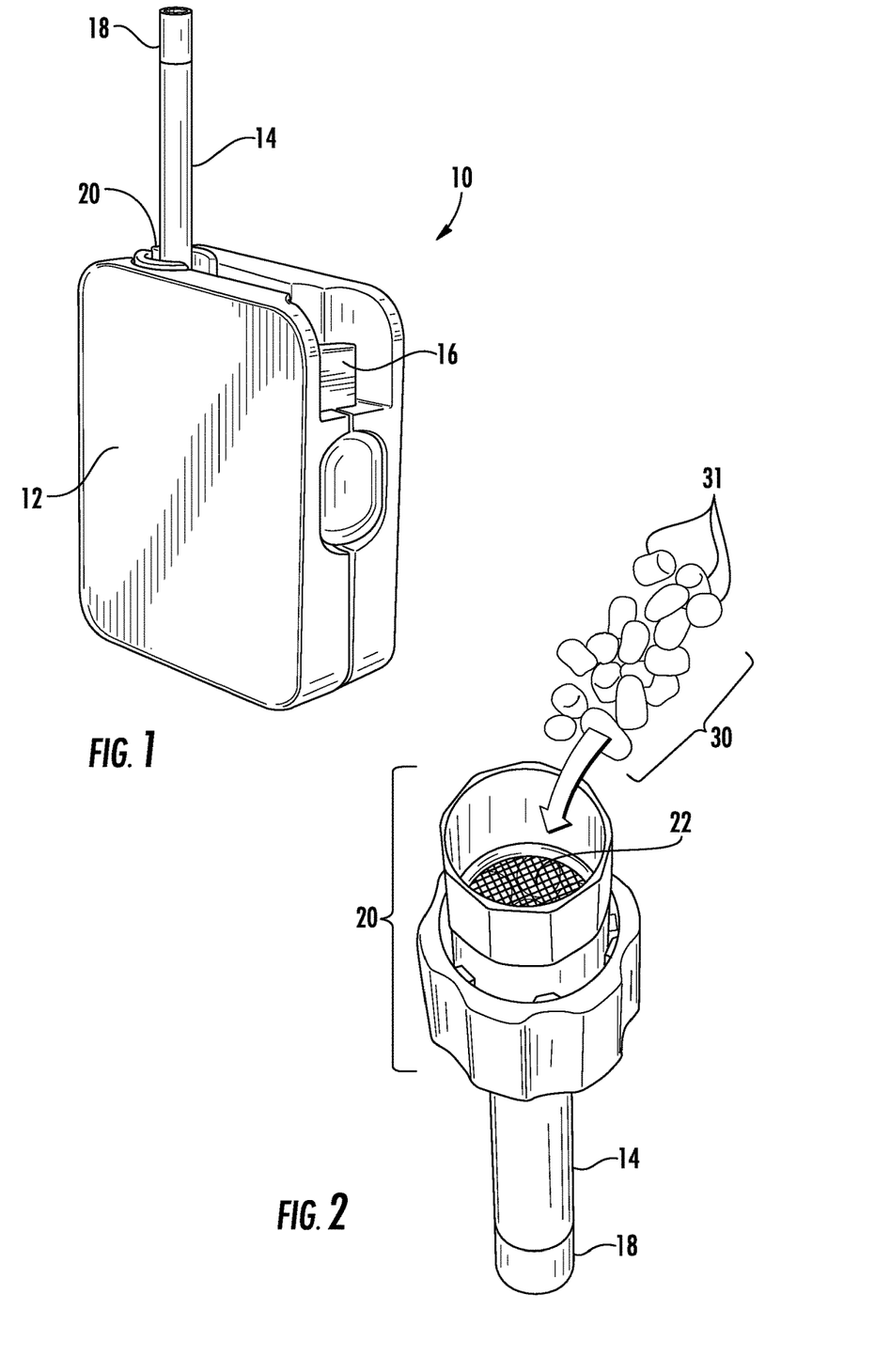
FIG. 1 is an environmental perspective view showing a typical vapor delivery device suitable for use with pellet substrates for vaporizing and delivering an aerosol according to the present invention.
FIG. 2 is an environmental perspective view showing a heating and vaporizing chamber of the vapor delivery device of FIG. 1 being filled with pellet substrates for vaporizing and delivering an aerosol according to the present invention.

An exemplary vapor delivery device, indicated generally by reference character 10, for use with pellet substrates for vaporizing and delivering an aerosol according to the present invention is shown in FIG. 1. By way of example and not limitation, a suitable vapor delivery device 10 is commercially known as Iolite® WISPR® and is available from Ogelsby & Butler of Carlow, Ireland. The device 10 comprises a housing 12, a vapor delivery chamber 14 extending outwardly from the housing 12 in the form of a generally hollow tube or stem, and an actuator 16 for activating the device between an inactive mode, a heating mode and a subsequent vapor delivery mode in a known manner. The device 10 further comprises a removable mouthpiece (not shown) that is attached to a free end 18 of the vapor delivery chamber 14 for delivering an aerosol containing flavoring, nicotine and/or an extract to a smoker. FIG. 2 shows a heating and vaporizing chamber 20 of the vapor delivery device 10. The heating and vaporizing chamber 20 is also commonly referred to as the "oven" of the device 10. The oven 20 is constructed so as to be in fluid (i.e., air) communication with the vapor delivery chamber 14 and is removably disposed within the housing 12 of the device 10.

In FIG. 2, the oven 20 is shown removed from the housing 12 of the vapor delivery device 10 and in an inverted position for being filled with one or more substrates, indicated generally by reference character 30, comprising material to be vaporized into an aerosol and delivered to a smoker. Consequently, the heating and vaporizing chamber 20 additionally functions as a substrate holder for the substrates 30. The oven 20 comprises a fine mesh screen 22 for preventing the substrates 30 from being drawn by inhalation of the user through the vapor delivery chamber 14 into the mouthpiece at the free end 18 of the vapor delivery chamber 14. The vapor delivery device 10 may further comprise a heat conductor (not shown) disposed within the housing 12 for preventing the substrates 30 from coming into direct contact with a heating element (not shown) of the device 10. The heating element may be powered by an electric (e.g., battery) or a combustible gas (e.g., butane) power source in a known manner and as further shown and described in U.S. Pat. No. 9,016,274 B1, the entire disclosure of which is incorporated herein by reference. Heating of the substrates 30 may occur as a result of conduction heating and/or convection heating depending on the particular type of vapor delivery device 10.

Substrates 30 are formed of a material that conforms to the size and shape of the heating and vaporizing chamber (i.e., oven) 20 of the vapor delivery device 10. As previously mentioned, a device 10 suitable for use with the substrates 30 is the Iolite® WISPR® vaporizer commercially available from Ogelsby & Butler of Carlow, Ireland. Other suitable devices include the handheld Iolite® vaporizer, likewise available from Ogelsby & Butler, the PAX® and PAX 2® handheld vaporizers available from PAX Labs, Inc. of San Francisco, Calif., USA, the VOLCANO desktop vaporizer available from the Storz & Bickel Company of Tuttlingen, Germany, the FIREFLY® handheld vaporizer available from Firefly Company of San Francisco, Calif., USA, the Ploom and Ploom TECH vaporizers available from Japan Tobacco Inc. of Tokyo, Japan and the IQOS tobacco heating system available from Phillip Morris International (PMI) of Lausanne, Switzerland, as well as others.

The aforementioned vapor delivery devices have a heating and vaporizing chamber that may be configured to receive the substrates 30. In particular, the substrates 30 can be easily deposited, commonly referred to as "loaded," into the heating and vaporizing chamber 20, for example by pouring or funneling. In addition, the substrates 30 can be easily and readily removed after use without leaving significant residue. In that regard, it has been determined that a substrate having a generally rounded shape, such as a generally spherical or generally semi-spherical shape, is particularly advantageous for filling and emptying the heating and vaporizing chambers of a vapor delivery device. Furthermore, a substrate having a generally rounded shape provides additional surface area for volatizing an aerosol former from the substrate to produce an aerosol containing flavoring, nicotine and/or an extract to be delivered to a smoker. For purposes of this written description of exemplary embodiments of the invention, substrates having the aforementioned generally rounded shape are referred to herein as "pellet-shaped" or "pellet" substrates.

Substrates 30 according to the invention comprise at least one, and preferably, a plurality of pellet substrates 31 formed of a semi-porous, substantially inert substance exhibiting a relatively high capability and capacity for absorption, commonly referred to as adsorption. The pellet substrates 31 preferably have adsorption surface areas greater than about 200 $m^2/g$ and up to about 3000 $m^2/g$. In the exemplary embodiments disclosed herein, the pellet substrates 31 are formed of carbon or alumina, and more preferably, activated carbon or activated alumina. However, any other porous or semi-porous, inert substance having a relatively high capability and capacity for absorption may be utilized. In a particularly advantageous embodiment, the pellet substrates 31 are formed of granular activated carbon manufactured from high quality crushed or ground coconut husks or shells, commercially referred to as coconut granular activated carbon ("coconut GAC") or coconut activated carbon. Suitable pellet substrates 31 include, but are not limited to coconut granular activated carbon commercially available from Calgon Carbon Corporation of Moon Township, Pa., USA, such as coconut granular activated carbon OLC, coconut granular activated carbon OVC, and coconut activated carbon 208C. Other suitable granular activated carbon pellet substrates 31 are commercially available from Cabot Corporation of Boston, Mass., USA under the trade name NORIT® GCN. The OLC, OLV and GCN granular activated carbon and the 208C activated carbon pellets are available in a variety of mesh sizes, and thus, surface areas. Other pellet substrates 31 comprising granular activated carbon manufactured from other substances having high absorption capability and capacity, such as charcoal, coal, coke and wood, are also suitable for use with the present invention. Suitable activated carbon substances may contain some crystalline silica. However, activated carbon and activated alumina substances suitable for use with the present invention should be essentially free of carcinogenic components or compounds. Regardless, the pellet substrates 31 are produced from a porous or semi-porous, substantially inert substance that is processed to have relatively small, low-volume pores to increase the surface area available for adsorption. As used herein, the term "adsorption" is intended to have the ordinary and customary meaning of "the adhesion of atoms, ions or molecules from a gas, liquid or dissolved solid to a surface." Similarly, the term "absorption" is intended to have its ordinary and customary meaning of "the process or action by which one thing or substance absorbs another."

Pellet substrates 31 according to the present invention can be formed by several different methods and may be formed from numerous different substrate materials and/or mixtures of substrate materials. Exemplary embodiments of suitable methods and suitable materials are disclosed and shown herein. However, it should be understood and appreciated equivalent methods and substrate materials, as well as others not specifically disclosed herein, are intended to be encompassed by the intended broad scope of the present invention. By way of example and not limitation, suitable materials for forming the pellet substrates 31 include granular activated carbon (GAC), coconut granular activated carbon, coconut activated carbon, charcoal, coal, coke or wood activated carbon, cellulose-based, starch-based and sugar-based substances, and powders, such as calcium carbonate, alumina, pure carbon, etc. Pellet substrates 31 may also be formed of organic plant material, for example, a cereal plant, such as millet. In examples provided herein, the substrate pellets 31 generally comprise activated alumina or activated carbon. As used herein, the term "activated alumina" and the term "activated carbon" are intended to include any form of alumina or carbon that has been processed to have small, low-volume pores that increase the surface area available for adsorption. An example of activated carbon is charcoal that has been treated, such as by heating, to increase its adsorptive power. Another example of activated carbon is coconut shell granulated activated charcoal (also referred to as "coconut shell activated carbon") that has been heated in the presence of steam so as to create open pores that increase adsorption. If desired, the pellet substrates 31 may further comprise a water soluble gum to provide increased adhesion of additives, as will be described. Suitable examples of activated alumina may be made from aluminum oxide ($Al_2O_3$).

An exemplary embodiment of a method for forming the pellet substrates 31 comprises a first step of combining the semi-porous base material, such as activated alumina, activated carbon or millet, with a liquid solution comprising an aerosol former admixed with flavoring, nicotine, tobacco powder and/or a tobacco extract. In a second step, the liquid solution is allowed to be adsorbed into the base material over a suitable period of time. In an optional third step, heat greater than the ambient temperature may be applied to accelerate the adsorption process without causing thermal degradation or other adverse effects. In yet another optional fourth step, the mixture of base material and liquid solution may be coated with a dry, solid coating of an inert powder, such as calcium carbonate, aluminum oxide, alumina, carbon or the like, as well as combinations thereof. The inert powder of the coating serves to promote adhesion of the liquid solution to the exposed surfaces of the base material, and thereby provides a relatively smooth, dry exterior surface, so that the pellet substrates 31 flow with reduced friction relative to one another for easily filling and removing the pellet substrates 31 from the heating and vaporizing chamber 20 of the vapor delivery device 10.

In another exemplary embodiment of a method for forming the pellet substrates 31, the activated alumina, activated carbon or millet is first coated with a liquid mixture comprising a water soluble gum, for example a relatively low viscosity cellulose gum, such as sodium carboxymethylcellulose (NaCMC), and distilled water. A suitable cellulose gum is sodium carboxymethylcellulose (NaCMC) type 7LF commercially available from Ashland Inc. of Covington, Ky., USA under the trade name Aqualon® CMC-7LF. The liquid mixture is allowed to absorb into the porous structure of the activated alumina, activated carbon or millet and to adsorb onto the exposed surfaces of the base material. The concentration of the liquid mixture is preferably between about 0.01% and about 5.0% cellulose gum. More preferably, the concentration of the liquid mixture is between about 0.01% and about 1.0% cellulose gum. In the examples provided herein, 0.2 grams of Aqualon® CMC-7LF was mixed with 100 grams of distilled water, resulting in a concentration of 0.2%. The liquid solution was applied to the exposed surfaces of activated alumina, activated carbon or millet granules and allowed to be absorbed into the porous structure. The remaining moisture was then removed by drying the coated base material in a heated environment, such as a heat exchanger or a heat chamber, at a temperature sufficient to remove the excess moisture in a reasonable period of time without any adverse effect. The temperature of the heated environment is preferably between about 100° F. and about 250° F.

The water soluble gum, such as a sodium carboxymethylcellulose (NaCMC) coating, serves to potentially eliminate or substantially reduce fracturing, cracking, chipping and/or dusting of the pellet substrates 31 as compared to activated alumina, activated carbon or millet granules that have not been coated. Surprisingly, it has been found that coating the activated alumina, activated carbon or millet granules with a mixture of NaCMC and distilled water does not adversely affect adsorption of the liquid solution comprising an aerosol former and at least one of a flavoring, nicotine, tobacco powder and/or a tobacco extract, such as a conventional e-liquid formulation. It has been confirmed that granular activated carbon (GAC) pellets with a sodium carboxymethylcellulose (NaCMC) coating typically adsorb at a ratio of 2 parts carbon to 1 part e-liquid solution, which is substantially the same as has been obtained with the uncoated activated carbon pellets. The water soluble gum may be a film-forming food grade gum, such as xanthan, guar, alginates, starches, locust beans, acacia, etc., which are expected to provide the same or similar benefit. Regardless, pellet substrates 31 that have been pre-coated with a water soluble gum, and in particular NaCMC, are referred to herein as "coated" or "treated" substrates. Pellet substrates 31 that are not pre-coated with a water soluble gum, and in particular NaCMC, are referred to herein as "uncoated" or "untreated" substrates.

Figure 3:
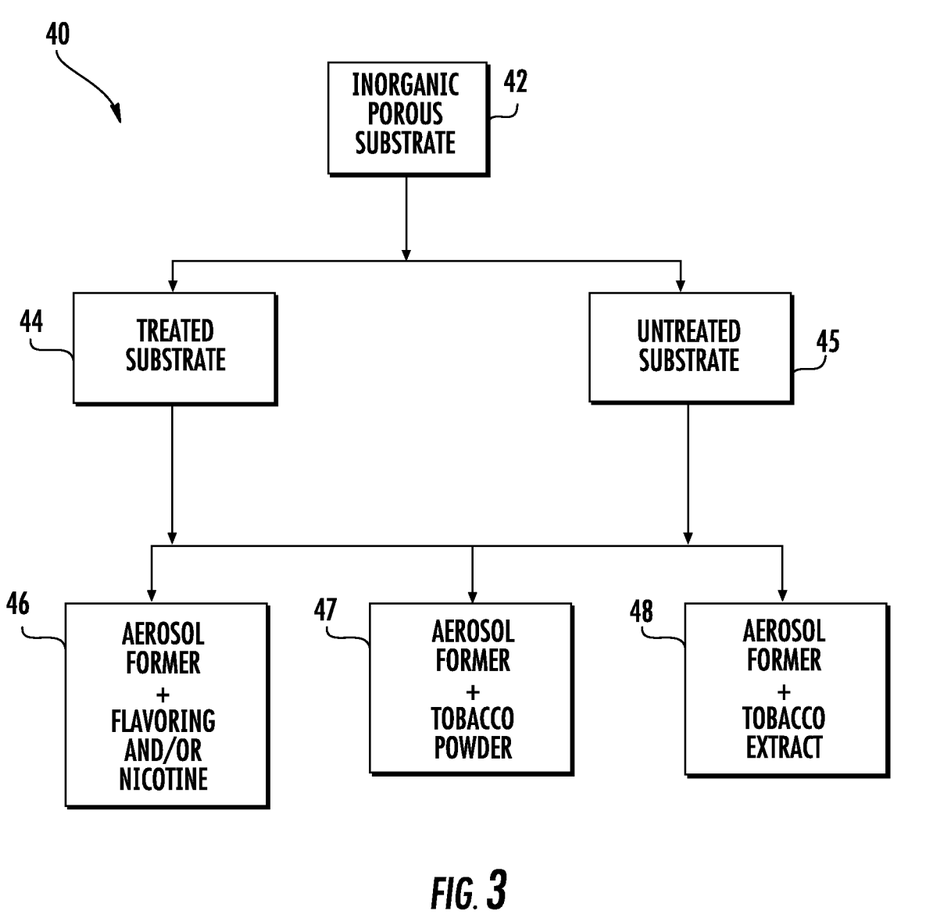
FIG. 3 is schematic flowchart depicting exemplary embodiments of pellet substrates for vaporizing and delivering an aerosol according to the present invention.

As previously mentioned pellet substrates 31 according to the present invention may further comprise pharmacologically or physiologically active agents and any desired additive, such as a therapeutic drug, a flavoring, nicotine, tobacco powder and/or an extract. FIG. 3 is a schematic flowchart depicting exemplary embodiments 40 of pellet substrates 31 configured for use with a vapor delivery device 10 for vaporizing and delivering an aerosol according to the present invention. As previously described, the pellet substrates 31 comprise a porous, or at least semi-porous, base material 42 formed from a substantially inert material, such as activated alumina, activated carbon or millet. The porous, inert base material 42 is either a treated base material 44 treated in the manner described herein with a water soluble gum pre-coating, or alternatively, is an untreated base material 45. Regardless, the treated base material 44 or the untreated base material 45 is further admixed with a liquid solution comprising an aerosol former and at least one of a flavoring and/or nicotine 46, an aerosol former and tobacco powder 47, or an aerosol former and tobacco extract 48. Consequently, pellet substrates 31 according to the present invention comprise at least three (3) types of treated pellet substrates (i.e., 44/46; 44/47; 44/48) and at least three (3) types of untreated pellet substrates (i.e., 45/46; 45/47; 45/48). However, the particular examples of pellet substrates 31 described herein are provided for purposes of explanation only and not by way of limitation.

The following specific examples of pellet substrates 31 have been found to be particularly well suited for use with a vapor delivery device 10 to vaporize and deliver an aerosol to a user, such as a patient or a smoker, in the manner contemplated by the present invention using the aforementioned methods comprising the various process steps of mixing, admixing, coating, applying, absorbing and/or adsorbing, and heating. The specific examples of pellet substrates 31 have been grouped together in the following Tables 1-16 by common composition and a variable component for purposes of ready comparison.

TABLE 1

| Example No. | Porous Inert Substrate | Aerosol Former+ |
| --- | --- | --- |
| 1 | 20 g Coconut GAC (12 × 30) | 5 g (70VG/30PG) |
| 2 | 20 g Coconut GAC (12 × 30) | 10 g (70VG/30PG) 1 g CaCO₃ Coating |

The pellet substrates 31 of Example 1 were formed by mixing in a glass flask about 20 grams by weight of Calgon Carbon coconut granular activated carbon (GAC) OLC 12×30 mesh pellets together with about 5 grams by weight of a liquid solution containing an aerosol former consisting of about 70% vegetable glycerin (VG) and about 30% propylene glycol (PG). The mixture was then heated to a temperature of between about 150° F. and about 200° F. for a time greater than about 4 hours by applying flame heat to the bottom of the flask. The liquid solution was rapidly adsorbed into the coconut GAC pellets. The pellets were allowed to cool and about 300 mg of the pellet substrates 31 were loaded into a vapor delivery device 10, namely an Iolite® butane heat vaporizer. The vaporizer was operated according to the manufacturer's specifications and the vaporizer delivered a substantial amount of aerosol with no appreciable off taste such that "good" taste was achieved.

The pellet substrates 31 of Example 2 were formed by mixing in a glass flask about 20 grams by weight of Calgon Carbon coconut granular activated carbon (GAC) OLC 12×30 mesh pellets together with about 10 grams by weight of a liquid solution containing an aerosol former consisting of about 70% vegetable glycerin (VG) and about 30% propylene glycol (PG). The mixture was then heated to a temperature of between about 150° F. and about 200° F. for about 1 hour by applying flame heat to the bottom of the flask. A residual amount of the liquid solution remained on the surface of the pellets. About 1 gram of an inert dry powder coating, namely calcium carbonate, was applied to the surface of the pellets so that the liquid solution was adsorbed into the porous pellets over time. The pellets were allowed to cool and about 600 mg of the pellet substrates 31 were loaded into a vapor delivery device 10, namely an Iolite® butane heat vaporizer. The vaporizer was operated according to the manufacturer's specifications and very good aerosol delivery with no appreciable off taste was achieved.

The foregoing examples of pellet substrate 31 demonstrated the efficacy of a liquid solution containing an aerosol former being adsorbed into pellets manufactured from coconut granular activated carbon (GAC). The following examples of pellet substrates 31 demonstrate the use of a liquid solution comprising an e-liquid containing an aerosol former admixed with nicotine and/or flavoring that is adsorbed into coconut granular activated carbon (GAC) pellets of various mesh sizes.

TABLE 2

| Example No. | Porous Inert Substrate | Aerosol Former+ |
| --- | --- | --- |
| 3 | 20 g Coconut GAC (12 × 30) | 10 g (70VG/30PG) Menthol Flavoring 1% Nicotine 0.5 g CaCO₃ Coating |
| 4 | 20 g Coconut GAC (12 × 30) w/16 Mesh Screen | 10 g (70VG/30PG) Menthol Flavoring 1% Nicotine |
| 5 | 40 g Coconut GAC (6 × 12) | 20 g (70VG/30PG) Menthol Flavoring 1% Nicotine |

The pellet substrates 31 of Example 3 were formed by mixing about 20 grams by weight of Calgon Carbon coconut granular activated carbon (GAC) OLC 12×30 mesh pellets together with about 10 grams by weight of an e-liquid solution containing an aerosol former consisting of about 70% vegetable glycerin (VG) and about 30% propylene glycol admixed with menthol flavoring and about 1% nicotine. A residual amount of the e-liquid solution remained on the surface of the pellets. About 0.5 grams of an inert dry powder coating, namely calcium carbonate, was applied to the surface of the pellet substrates 31 so that the liquid solution was adsorbed into the pellet substrates over time.

The pellet substrates 31 of Example 4 were formed by mixing the remaining portion of about 20 grams by weight of Calgon Carbon coconut granular activated carbon (GAC) OLC 12×30 mesh pellets screened through a 16 mesh screen together with about 10 grams by weight of an e-liquid solution containing an aerosol former consisting of about 70% vegetable glycerin (VG) and about 30% propylene glycol admixed with menthol flavoring and about 1% nicotine. The e-liquid solution was then allowed to be adsorbed into the pellets over time.

The pellet substrates 31 of Example 5 were formed by mixing about 40 grams by weight of Calgon Carbon coconut granular activated carbon (GAC) 208C 6×12 mesh pellets together with about 20 grams by weight of an e-liquid solution containing an aerosol former consisting of about 70% vegetable glycerin (VG) and about 30% propylene glycol (PG) admixed with menthol flavoring and about 1% nicotine. The mixture was then heated at about 48° C. for about 6 hours to aid adsorption of the e-liquid solution into the pellets. The pellets were allowed to cool and about 200 mg of the pellet substrates 31 were loaded into a vapor delivery device 10, namely an Iolite® butane heat vaporizer. The vaporizer was operated according to the manufacturer's specifications and very good aerosol delivery with no appreciable off taste was achieved.

TABLE 3

| Example No. | Porous Inert Substrate | Aerosol Former+ |
|---|---|---|
| 6 | 14 g Coconut GAC (8 × 16) | 6 g (100PG) |
| 7 | 14 g Coconut GAC (8 × 16) | 6 g (70VG/30PG) |
| 8 | 14 g Coconut GAC (8 × 16) | 6 g (100VG) |

The pellet substrates 31 of Example 6 were formed by mixing about 14 grams by weight of Cabot Corporation coconut granular activated carbon (GAC) NORIT® GCN 816G 8×16 mesh pellets together with about 6 grams by weight of a liquid solution containing an aerosol former consisting of about 100% propylene glycol (PG).

The pellet substrates 31 of Example 7 were formed by mixing about 14 grams by weight of Cabot Corporation coconut granular activated carbon (GAC) NORIT® GCN 816G 8×16 mesh pellets together with about 6 grams by weight of a liquid solution containing an aerosol former consisting of about 70% vegetable glycerin (VG) and about 30% propylene glycol (PG).

The pellet substrates 31 of Example 8 were formed by mixing about 14 grams by weight of Cabot Corporation coconut granular activated carbon (GAC) NORIT® GCN 816G 8×16 mesh pellets together with about 6 grams by weight of a liquid solution containing an aerosol former consisting of about 100% vegetable glycerin (VG).

TABLE 4

| Example No. | Porous Inert Substrate | Aerosol Former+ |
|---|---|---|
| 9 | 30 g Coconut GAC (8 × 16) | 15 g (70VG/30PG) 3% Menthol Flavoring |
| 10 | 30 g Coconut GAC (8 × 16) | 15 g (70VG/30PG) 3% Menthol Flavoring 0.6% Nicotine |
| 11 | 30 g Coconut GAC (8 × 16) | 15 g (70VG/30PG) 3% Menthol Flavoring 1.2% Nicotine |
| 12 | 30 g Coconut GAC (8 × 16) | 15 g (70VG/30PG) 3% Menthol Flavoring 2.4% Nicotine |

The pellet substrates 31 of Example 9 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with menthol flavoring at about 3%.

The pellet substrates 31 of Example 10 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with about 3% menthol flavoring and 0.6% nicotine.

The pellet substrates 31 of Example 11 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with about 3% menthol flavoring and 1.2% nicotine.

The pellet substrates 31 of Example 12 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with about 3% menthol flavoring and 2.4% nicotine.

TABLE 5

| Example No. | Porous Inert Substrate | Aerosol Former+ |
|---|---|---|
| 13 | 30 g Coconut GAC (8 × 16) | 15 g (70VG/30PG) 4% Tobacco Flavoring |
| 14 | 30 g Coconut GAC (8 × 16) | 15 g (70VG/30PG) 4% Tobacco Flavoring 0.6% Nicotine |
| 15 | 30 g Coconut GAC (8 × 16) | 15 g (70VG/30PG) 4% Tobacco Flavoring 1.2% Nicotine |
| 16 | 30 g Coconut GAC (8 × 16) | 15 g (70VG/30PG) 4% Tobacco Flavoring 2.4% Nicotine |

The pellet substrates 31 of Example 13 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with tobacco flavoring at about 4%.

The pellet substrates 31 of Example 14 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with tobacco flavoring at about 4% and nicotine at about 0.6%.

The pellet substrates 31 of Example 15 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with tobacco flavoring at about 4% and nicotine at about 1.2%.

The pellet substrates 31 of Example 16 were formed by mixing about 30 grams by weight of Cabot Corporation coconut granular activated carbon (GAC) NORIT® GCN 816G 8×16 mesh pellets together with about 15 grams by weight of an e-liquid solution containing an aerosol former consisting of about 70% vegetable glycerin (VG) and about 30% propylene glycol (PG) admixed with tobacco flavoring at about 4% and nicotine at about 2.4%.

TABLE 6

| Example No. | Porous Inert Substrate | Aerosol Former+ |
| --- | --- | --- |
| 17 | 15 g Coconut GAC (8 × 16) | 7.5 g (70VG/30PG)<br>5% Tobacco Flavoring<br>1.2% Nicotine |
| 18 | 15 g Coconut GAC (8 × 16) | 7.5 g (70VG/30PG)<br>10% Tobacco Flavoring<br>1.2% Nicotine |
| 19 | 15 g Coconut GAC (8 × 16) | 7.5 g (70VG/30PG)<br>20% Tobacco Flavoring<br>1.2% Nicotine |

The pellet substrates 31 of Example 17 were formed by mixing about 15 grams by weight of Cabot Corporation coconut granular activated carbon (GAC) NORIT® GCN 816G 8×16 mesh pellets together with about 7.5 grams by weight of an e-liquid solution containing an aerosol former consisting of about 70% vegetable glycerin (VG) and about 30% propylene glycol (PG) admixed with tobacco flavoring at about 5% and nicotine at about 1.2%.

The pellet substrates 31 of Example 18 were formed by mixing about 15 grams by weight of Cabot Corporation coconut granular activated carbon (GAC) NORIT® GCN 816G 8×16 mesh pellets together with about 7.5 grams by weight of an e-liquid solution containing an aerosol former consisting of about 70% vegetable glycerin (VG) and about 30% propylene glycol (PG) admixed with tobacco flavoring at about 10% and nicotine at about 1.2%.

The pellet substrates 31 of Example 19 were formed by mixing about 15 grams by weight of Cabot Corporation coconut granular activated carbon (GAC) NORIT® GCN 816G 8×16 mesh pellets together with about 7.5 grams by weight of an e-liquid solution containing an aerosol former consisting of about 70% vegetable glycerin (VG) and about 30% propylene glycol (PG) admixed with tobacco flavoring at about 20% and nicotine at about 1.2%.

TABLE 7

| Example No. | Porous Inert Substrate | Aerosol Former+ |
| --- | --- | --- |
| 20 | 15 g Coconut GAC (8 × 16) | 7.5 g (70VG/30PG)<br>3% Menthol Flavoring<br>1.2% Nicotine |
| 21 | 15 g Coconut GAC (6 × 12) | 7.5 g (70VG/30PG)<br>3% Menthol Flavoring<br>1.2% Nicotine |
| 22 | 18 g Coconut GAC (12 × 40) | 9 g (70VG/30PG)<br>3% Menthol Flavoring<br>1.2% Nicotine |

The pellet substrates 31 of Example 20 were formed by mixing about 15 grams by weight of Cabot Corporation NORIT® GCN 816G 8×16 mesh coconut shell based granular activated carbon (GAC) pellets together with about 7.5 grams by weight of an e-liquid solution containing an aerosol former consisting of about 70% vegetable glycerin (VG) and about 30% propylene glycol (PG) admixed with menthol flavoring at about 3% and nicotine at about 1.2%.

The pellet substrates 31 of Example 21 were formed by mixing about 15 grams by weight of Cabot Corporation NORIT® GCN 612G 6×12 mesh coconut shell based granular activated carbon (GAC) pellets together with about 7.5 grams by weight of an e-liquid solution containing an aerosol former consisting of about 70% vegetable glycerin (VG) and about 30% propylene glycol (PG) admixed with menthol flavoring at about 3% and nicotine at about 1.2%.

The pellet substrates 31 of Example 22 were formed by mixing about 18 grams by weight of Cabot Corporation NORIT® GCN 1240G 12×40 mesh coconut shell based granular activated carbon (GAC) pellets together with about 9 grams by weight of an e-liquid solution containing an aerosol former consisting of about 70% vegetable glycerin (VG) and about 30% propylene glycol (PG) admixed with menthol flavoring at about 3% and nicotine at about 1.2%. The e-liquid solution was allowed to soak into the pellets for at least about 12 hours until fully adsorbed. The pellet substrates 31 were loaded into a vapor delivery device 10, namely an Iolite® butane heat vaporizer. The vaporizer was operated according to the manufacturer's specifications and very good aerosol delivery with no appreciable off taste was achieved.

TABLE 8

| Example No. | Porous Inert Substrate | Aerosol Former+ |
| --- | --- | --- |
| 23 | 16 g Coconut GAC (6 × 12)<br>Mixed With/Added To:<br>16 g Coconut GAC (6 × 12) | 4 g Menthol Crystals<br>(70VG/30PG)<br>Menthol Flavoring<br>Nicotine |

The substrates 30 of Example 23 were formed by mixing about 16 grams by weight of Cabot Corporation NORIT® GCN 612G 6×12 mesh coconut shell based granular activated carbon (GAC) pellets together with about 4 grams by weight of menthol crystals. Menthol flavoring was infused into the pellet substrates 31 by mixing the menthol crystals together with the pellets and placing the mixture into a closed container in which the temperature was raised to between about 150° F. and about 200° F. over a period of time between about 2 hours and about 4 hours. Menthol from the menthol crystals completely vaporized and was adsorbed by the coconut GAC pellets. Pellet substrates 31 according to this example may be added to or mixed with pellet substrates 31 comprising an aerosol former (e.g., vegetable glycerin/propylene glycol) admixed with flavoring and/or nicotine to provide a menthol flavor boost. Likewise, other volatile aromas and/or flavoring, such as coffee, tea, cocoa, oak, hickory and the like, may be infused into granular activated carbon (GAC) based pellet substrates.

TABLE 9

| Example No. | Porous Inert Substrate | Aerosol Former+ |
| --- | --- | --- |
| 24 | 1360 g Coconut GAC (6 × 12) | 680 g (70VG/30PG)<br>Menthol Flavoring |
| 25 | 1360 g Coconut GAC (6 × 12) | 680 g (70VG/30PG)<br>Menthol Flavoring<br>1.2% Nicotine |
| 26 | 1360 g Coconut GAC (6 × 12) | 680 g (70VG/30PG)<br>Menthol Flavoring<br>1.8% Nicotine |

The pellet substrates 31 of Example 24 were formed by mixing about 1360 grams by weight of Carbon Activated Corporation coconut granular activated carbon (GAC) 6×12 mesh pellets together with about 680 grams by weight of an e-liquid solution containing an aerosol former consisting of about 70% vegetable glycerin (VG) and about 30% propylene glycol (PG) admixed with menthol flavoring.

The pellet substrates 31 of Example 25 were formed by mixing about 1360 grams by weight of Carbon Activated Corporation coconut granular activated carbon (GAC) 6×12 mesh pellets together with about 680 grams by weight of an e-liquid solution containing an aerosol former consisting of about 70% vegetable glycerin (VG) and about 30% propylene glycol (PG) admixed with menthol flavoring and nicotine at about 1.2%.

The pellet substrates 31 of Example 26 were formed by mixing about 1360 grams by weight of Carbon Activated Corporation coconut granular activated carbon (GAC) 6×12 mesh pellets together with about 680 grams by weight of an e-liquid solution containing an aerosol former consisting of about 70% vegetable glycerin (VG) and about 30% propylene glycol (PG) admixed with menthol flavoring and nicotine at about 1.8%.

In each of the foregoing Examples 24-26 the pellets adsorbed all of the e-liquid solution to form dry pellet substrates 31.

TABLE 10

| Example No. | Porous Inert Substrate | Aerosol Former+ |
| --- | --- | --- |
| 27 | 1360 g Coconut GAC (6 × 12) | 680 g (70VG/30PG) Tobacco Flavoring |
| 28 | 1360 g Coconut GAC (6 × 12) | 680 g (70VG/30PG) Tobacco Flavoring 1.2% Nicotine |
| 29 | 1360 g Coconut GAC (6 × 12) | 680 g (70VG/30PG) Tobacco Flavoring 1.8% Nicotine |

The pellet substrates 31 of Example 27 were formed by mixing about 1360 grams by weight of Carbon Activated Corporation coconut granular activated carbon (GAC) 6×12 mesh pellets together with about 680 grams by weight of an e-liquid solution containing an aerosol former consisting of about 70% vegetable glycerin (VG) and about 30% propylene glycol (PG) admixed with tobacco flavoring.

The pellet substrates 31 of Example 28 were formed by mixing about 1360 grams by weight of Carbon Activated Corporation coconut granular activated carbon (GAC) 6×12 mesh pellets together with about 680 grams by weight of an e-liquid solution containing an aerosol former consisting of about 70% vegetable glycerin (VG) and about 30% propylene glycol (PG) admixed with tobacco flavoring and nicotine at about 1.2%.

The pellet substrates 31 of Example 29 were formed by mixing about 1360 grams by weight of Carbon Activated Corporation coconut granular activated carbon (GAC) 6×12 mesh pellets together with about 680 grams by weight of an e-liquid solution containing an aerosol former consisting of about 70% vegetable glycerin (VG) and about 30% propylene glycol (PG) admixed with tobacco flavoring and nicotine at about 1.8%.

In each of the foregoing Examples 27-29 the pellets adsorbed all of the e-liquid solution to form dry pellet substrates 31.

TABLE 11

| Example No. | Porous Inert Substrate | Aerosol Former+ |
| --- | --- | --- |
| 30 | 32 g Coconut GAC (6 × 12) | 16 g (70VG/30PG) 5 g Tobacco Powder |
| 31 | 32 g Coconut GAC (6 × 12) | 16 g (70VG/30PG) 8 g Tobacco Blend Powder |
| 32 | 32 g Coconut GAC (6 × 12) | 16 g (70VG/30PG) 11.5 g Distilled Water 5 g Coffee Powder |

The pellet substrates 31 of Example 30 were formed by mixing about 32 grams by weight of Carbon Activated Corporation coconut granular activated carbon (GAC) 6×12 mesh pellets together with about 16 grams by weight of an e-liquid solution containing an aerosol former consisting of about 70% vegetable glycerin (VG) and about 30% propylene glycol (PG) admixed with about 5 grams by weight of tobacco powder. The tobacco powder was finely-ground to less than 20 microns, and more preferably, less than 10 microns. The pellets adsorbed all of the e-liquid solution to form dry pellet substrates 31.

The pellet substrates 31 of Example 31 were formed by mixing about 32 grams by weight of Carbon Activated Corporation coconut granular activated carbon (GAC) 6×12 mesh pellets together with about 16 grams by weight of an e-liquid solution containing an aerosol former consisting of about 70% vegetable glycerin (VG) and about 30% propylene glycol (PG) admixed with about 8 grams by weight of tobacco blend powder. The tobacco powder was finely-ground to less than 20 microns, and more preferably, less than 10 microns. The pellets adsorbed all of the e-liquid solution to form dry pellet substrates 31.

The pellet substrates 31 of Example 32 were formed by mixing about 32 grams by weight of Carbon Activated Corporation coconut granular activated carbon (GAC) 6×12 mesh pellets together with about 16 grams by weight of an e-liquid solution containing an aerosol former consisting of about 70% vegetable glycerin (VG) and about 30% propylene glycol (PG) admixed with about 11.5 grams by weight of distilled water and about 5 grams by weight of coffee powder. The liquid solution was adsorbed into the pellets and the pellets were dried at a temperature of about 150° F. to remove any residual moisture.

It should be noted that any dry plant (herbal) material powder, such as coffee powder, tea powder cocoa powder and marijuana powder may be substituted for the tobacco powder in the foregoing examples.

TABLE 12

| Example No. | Porous Inert Substrate | Aerosol Former+ |
| --- | --- | --- |
| 33 | 50 g 1/16" AA (7 × 12) | 25 g (70VG/30PG) Tobacco Flavoring 1.8% Nicotine |
| 34 | 55.2 g 1/16" AA (7 × 12) | 27.6 g (70VG/30PG) Menthol Flavoring 1.8% Nicotine |

The pellet substrates 31 of Example 33 were formed by mixing about 50 grams by weight of UOP Honeywell D-201 1/16" diameter spherical activated alumina (AA) 7×12 mesh pellets together with about 25 grams by weight of an e-liquid solution containing an aerosol former consisting of about 70% vegetable glycerin (VG) and about 30% propylene glycol (PG) admixed with tobacco flavoring and nicotine at about 1.8%.

The pellet substrates 31 of Example 34 were formed by mixing about 55.2 grams by weight of UOP Honeywell D-201 1/16" diameter spherical activated alumina (AA) 7×12 mesh pellets together with about 27.6 grams by weight of an e-liquid solution containing an aerosol former consisting of about 70% vegetable glycerin (VG) and about 30% propylene glycol (PG) admixed with menthol flavoring and nicotine at about 1.8%.

In each of the foregoing Examples 33-34 the pellets adsorbed all of the e-liquid solution to form dry pellet substrates 31. In addition, these pellet substrates 31 delivered an excellent volume of aerosol and a satisfying flavor when used in a dry plant (herbal) material type vaporizer.

TABLE 13

| Example No. | Porous Inert Substrate | Aerosol Former+ |
|---|---|---|
| 35 | 50 g Coconut GAC (6 × 12) | 20 g Mixture: 0.2 g NaCMC and 100 g Distilled Water |
| 36 | 50 g 1/16" AA (7 × 12) | 30 g Mixture: 0.2 g NaCMC and 100 g Distilled Water |

The pellet substrates 31 of Example 35 were formed by coating about 50 grams by weight of Carbon Activated Corporation coconut granular activated carbon (GAC) 6×12 mesh pellets with about 20 grams by weight of a mixture comprising about 0.2 grams by weight of Ashland Inc. Aqualon® sodium carboxymethylcellulose (NaCMC) type 7-LF (CMC-7LF) together with about 100 grams by weight of distilled water. The liquid solution was allowed to absorb into and adsorb onto the porous structure of the activated carbon. The remaining excess moisture was removed by drying the coated pellets in a heated environment at a temperature of about 150° F. for about 24 hours.

The pellet substrates 31 of Example 36 were formed by coating about 50 grams by weight of UOP Honeywell D-201 1/16" diameter spherical activated alumina (AA) 7×12 mesh pellets with about 30 grams by weight of a mixture comprising about 0.2 grams by weight of Ashland Inc. Aqualon® sodium carboxymethylcellulose (NaCMC) type 7-LF (CMC-7LF) together with about 100 grams by weight of distilled water. The liquid solution was allowed to absorb into and adsorb onto the porous structure of the activated alumina. The remaining excess moisture was removed by drying the coated pellets in a heated environment at a temperature of about 150° F. for about 24 hours.

TABLE 14

| Example No. | Porous Inert Substrate | Aerosol Former+ |
|---|---|---|
| 37 | 20 g Coconut GAC (6 × 12) Treated With NaCMC/H$_2$O | 10 g (70VG/30PG) Menthol Flavoring 1.8% Nicotine |
| 38 | 20 g 1/16" AA (7 × 12) Treated With NaCMC/H$_2$O | 10 g (70VG/30PG) Menthol Flavoring 1.8% Nicotine |

The pellet substrates 31 of Example 37 were formed by mixing about 20 grams by weight of Carbon Activated Corporation coconut granular activated carbon (GAC) 6×12 mesh pellets treated with the mixture of Ashland Inc. Aqualon® CMC-7LF (NaCMC) and distilled water described with reference to Example 35 and Example 36 with about 10 grams by weight of an e-liquid solution containing an aerosol former consisting of about 70% vegetable glycerin (VG) and about 30% propylene glycol (PG) admixed with menthol flavoring and nicotine at about 1.8%.

The pellet substrates 31 of Example 38 were formed by mixing about 20 grams by weight of UOP Honeywell D-201 1/16" diameter spherical activated alumina (AA) 7×12 mesh pellets treated with the mixture of Ashland Inc. Aqualon® CMC-7LF (NaCMC) and distilled water described with reference to Example 35 and Example 36 with about 10 grams by weight of an e-liquid solution containing an aerosol former consisting of about 70% vegetable glycerin (VG) and about 30% propylene glycol (PG) admixed with menthol flavoring and nicotine at about 1.8%.

TABLE 15

| Example No. | Porous Inert Substrate | Aerosol Former+ |
|---|---|---|
| 39 | 16 g Coconut GAC (6 × 12) Treated With NaCMC/H$_2$O | 8 g (70VG/30PG) 4 g Tobacco Blend Powder |
| 40 | 31 g 1/16" AA (7 × 12) Treated With NaCMC/H$_2$O | 15.5 g (70VG/30PG) 7.8 g Tobacco Blend Powder |

The pellet substrates 31 of Example 39 were formed by mixing about 16 grams by weight of Carbon Activated Corporation coconut granular activated carbon (GAC) 6×12 mesh pellets treated with the mixture of Ashland Inc. Aqualon® CMC-7LF (NaCMC) and distilled water described with reference to Example 35 and Example 36 with about 8 grams by weight of an e-liquid solution containing an aerosol former consisting of about 70% vegetable glycerin (VG) and about 30% propylene glycol (PG) admixed with about 4 grams by weight of tobacco blend powder.

The pellet substrates 31 of Example 40 were formed by mixing about 31 grams by weight of UOP Honeywell D-201 1/16" diameter spherical activated alumina (AA) 7×12 mesh pellets treated with the mixture of Ashland Inc. Aqualon® CMC-7LF (NaCMC) and distilled water described with reference to Example 35 and Example 36 with about 15.5 grams by weight of an e-liquid solution containing an aerosol former consisting of about 70% vegetable glycerin (VG) and about 30% propylene glycol (PG) admixed with about 7.8 grams by weight of tobacco blend powder.

TABLE 16

| Example No. | Porous Inert Substrate | Aerosol Former+ |
|---|---|---|
| 41 | 20 g Coconut GAC (6 × 12) | 10 g Mixture: 20 g (70VG/30PG) 5.5 g Oriental Tobacco Extract 7.8 g Flue Cured Extract |
| 42 | 20 g 1/16" AA (7 × 12) | 10 g Mixture: 20 g (70VG/30PG) 5.5 g Oriental Tobacco Extract 7.8 g Flue Cured Extract |

The pellet substrates 31 of Example 41 were formed by mixing about 20 grams by weight of Carbon Activated Corporation coconut granular activated carbon (GAC) 6×12 mesh pellets with about 10 grams by weight of a mixture of a liquid solution formed from about 20 grams by weight of an e-liquid solution containing an aerosol former consisting of about 70% vegetable glycerin (VG) and about 30% propylene glycol (PG) admixed with about 5.5 grams by weight of oriental tobacco extract and 7.8 grams by weight of a flue cured extract.

The pellet substrates 31 of Example 42 were formed by mixing about 20 grams by weight of UOP Honeywell D-201 1/16" diameter spherical activated alumina (AA) 7×12 mesh pellets with about 10 grams by weight of a mixture of a liquid solution formed from about 20 grams by weight of an e-liquid solution containing an aerosol former consisting of about 70% vegetable glycerin (VG) and about 30% propylene glycol (PG) admixed with about 5.5 grams by weight of oriental tobacco extract and 7.8 grams by weight of a flue cured extract.

It should be noted that extracts of other dry plant (herbal) material, such as coffee, tea and marijuana may be substituted for the tobacco extracts in the foregoing examples.

Substances, components, elements, materials and mixtures suited for use with the aforementioned pellet substrates according to the present invention include, but are not limited to, the following:

(a) calcium carbonate 5970 available from Specialty Minerals, Inc.;

(b) aerosol formers in solid, semisolid, or liquid form, including polyhydric alcohols and mixtures of polyhydric alcohols, such as glycerin, vegetable glycerin (VG), glycerol, polyethylene glycol (PEG400), propylene glycol, 1,3-butylene glycol, triethylene glycol, glycerol esters, such as triacetin, propylene carbonate, and mixtures thereof, as well as aliphatic esters of mono-, di-, or poly-carboxylic acids, such as methyl stearate, dimethyl dodecandioate, dimethyl tetradecandioate, and others;

(c) organic plant material, for example, tobacco, marijuana, coffee, tea, etc., in a whole, cut, chopped, ground or powder form, and plant extracts, such as a tobacco extract and marijuana extract; and (d) filler material, for example calcium carbonate, alumina (synthetically produced aluminum oxide), activated carbon powder, graphite powder, combinations thereof, and other similar materials that will not ignite or burn at the vaporization temperatures of the aerosol agent and aerosol forming agent.

The 6×12, 8×16, 12×30 and 12×40 mesh coconut shell based granulated activated carbon (GAC) pellets as well as the 7×12 mesh 1/16" diameter spherical activated alumina (AA) pellets disclosed herein are well suited for use with certain vapor delivery devices, such as the Iolite® butane heat vaporizer. However, pellet substrates 31 having different mesh sizes may be better suited for use with other vapor delivery devices 10, and in particular, vapor delivery devices powered by an electronic (e.g., battery) power source. As such, the mesh sizes of the pellet substrates 31 disclosed herein are merely exemplary and provided for purposes of explanation and illustration only.

The following materials have been found to be advantageous for forming pellet substrates 31 that are particularly well suited for use with vapor delivery devices 10 comprising a heating and vaporizing chamber, or oven 20 intended to operate at a temperature sufficient to produce an aerosol with causing thermal degradation or other adverse effects to the pellet substrates 31.

(A) Activated carbon, such as coconut shell granular activated carbon (GAC) having a mesh size between about 4 and about 30, preferably between about 6 and about 20, in accordance with U.S.A. Standard Sieves ASTME Specification E-11.

(B) Activated alumina having a mesh size between about 4 and about 30, preferably between about 6 and about 20, in accordance with U.S.A. Standard Sieves ASTME Specification E-11.

(C) Hulled millet grains or similar grains, such as rice, milo, corn, wheat, barley, oats, etc.

(D) A tobacco extract mixture comprising oriental tobacco extract at about 10.2% by weight, flue cured tobacco extract at about 15.7% by weight, aerosol former (e.g., 70VG/30PG) at about 37.0% by weight and distilled water at about 37.0% by weight.

(E) A liquid hydrocolloid gum solution, preferably food grade, comprising Aqualon® CMC-7LF at about 0.5% by weight and distilled water at about 99.5% by weight mixed together until the hydrocolloid gum is entirely dissolved and not visible.

(F) A tobacco powder blend comprising flue cured, burley and/or oriental tobacco milled to a very fine particle size less than about 20 microns, and preferably less than about 10 microns.

The materials described above were used to produce the following examples of pellet substrates 31 according to the present invention that are particularly well suited for use with a vapor delivery device 10, such as a heat-not-burn (HNB) type vapor delivery device.

Example 1

UOP Honeywell D-201 1/16" diameter spherical activated alumina (AA) 7×12 mesh pellets at about 50% by weight admixed with the tobacco extract mixture (D) at about 50% by weight. The liquid tobacco extract mixture is applied to the activated alumina pellets while stirring or mixing. The activated alumina pellets and tobacco extract mixture are then dried at approximately 150° F. until the liquid thoroughly penetrates the pellets and creates an essentially dry surface.

Example 2

Jacobi CX coconut shell based granular activated carbon (GAC) 6×12 mesh pellets at about 50% by weight admixed with the tobacco extract mixture (D) at about 50% by weight. The liquid tobacco extract mixture is applied to the activated carbon pellets while stirring or mixing. The activated carbon pellets and tobacco extract mixture are then dried at approximately 150° F. until the liquid thoroughly penetrates the pellets and creates an essentially dry surface.

Example 3

Jacobi CX coconut shell based granular activated carbon (GAC) 6×12 mesh pellets at about 48.4% by weight admixed with the tobacco extract mixture (D) at about 24.2% by weight, 70VG/30PG aerosol former at about 15.3% by weight and the tobacco powder blend (F) at about 12.2%. The liquid tobacco extract mixture and the aerosol former are applied to the activated carbon pellets while agitating by stirring or in a rotating drum. The tobacco powder blend is then added and the activated carbon pellets and tobacco powder blend are then dried at approximately 150° F. until the surface of the pellets is essentially dry.

Example 4

Jacobi CX coconut shell based granular activated carbon (GAC) 6×12 mesh pellets at about 57% by weight admixed with 70VG/30PG aerosol former at about 28.5% by weight and the tobacco powder blend (F) at about 14.4%. The liquid aerosol former is applied to the activated carbon pellets while stirring or mixing. The tobacco powder blend is then added and the activated carbon pellets and tobacco powder blend are then dried at approximately 150° F. until the surface of the pellets is essentially dry.

Example 5

UOP Honeywell D-201 1/16" diameter spherical activated alumina (AA) 7×12 mesh pellets at about 62.5% by weight admixed with the liquid hydrocolloid gum solution (E) at about 37.5% by weight. The liquid hydrocolloid gum solution is slowly mixed with the activated alumina pellets. The activated alumina pellets coated with the liquid hydrocolloid gum solution are then dried at approximately 150° F. until the surface of the pellets is essentially dry. A tobacco extract and/or a tobacco powder with aerosol former may then be added by agitation to coat the activated alumina pellets.

Example 6

Jacobi CX coconut shell based granular activated carbon (GAC) 6×12 mesh pellets at about 60.6% by weight admixed with the liquid hydrocolloid gum solution (E) at about 39.4% by weight. The liquid hydrocolloid gum solution is slowly or periodically mixed with the activated carbon pellets while the activated carbon pellets coated with the liquid hydrocolloid gum solution is dried at approximately 150° F. over a period of about 24 hours. A tobacco extract and/or a tobacco powder with aerosol former may then be added by agitation to coat the activated carbon pellets.

Example 7

Hulled millet grains (C) at about 40 grams coated with the tobacco extract mixture (D) at about 5 grams, 70VG/30PG aerosol former at about 2.5 grams and the tobacco powder blend (F) at about 3.46 grams. The hulled millet grains are coated with the tobacco extract mixture, aerosol former and tobacco powder blend and dried at approximately 150° F. until the surface of the grains is essentially dry. If desired, the hulled millet grains may be pre-coated with a water soluble gum, such as sodium carboxymethyl cellulose (NaCMC), which is preferably food grade. As previously mentioned, other grains, such as rice, milo, corn, wheat, barley, oats, etc. may be used.

Example 8

Cellulose absorbent paper or blotting paper free of additives, such as 13616 cellulose paper commercially available from EMI Specialty Paper of Redding, Conn. at about 5 grams mixed with the tobacco extract mixture at about 5 grams, 70VG/30PG aerosol former at about 2.5 grams, and the tobacco powder blend at about 1.26 grams until the cellulose paper absorbs the tobacco extract mixture, aerosol former and tobacco powder blend. The cellulose paper is the dried at approximately 150° F. until the surface of the cellulose paper is essentially dry. If desired, the cellulose paper may be pre-coated with a water soluble gum, such as sodium carboxymethyl cellulose (NaCMC), which is preferably food grade. The cellulose paper may have any desired size and shape, such as a generally flat disc shape, suitable for use with a particular vapor delivery device 10.

In other embodiments, activated alumina pellets, activated carbon pellets or hulled millet grains may be admixed with an aerosol former (e.g., 70VG/30PG) and a tobacco extract mixture and then blended with flakes of tobacco of about 1 to 3 millimeters in size.

In other embodiments, the activated alumina pellets, activated carbon pellets or hulled millet grains of the foregoing examples may be disposed within a semi-porous container made of a heat conductive material, such as a semi-porous aluminum container formed from an expanded aluminum that is at least about 50% heat conductive. The semi-porous, heat conductive container is preferably configured (i.e., sized and shaped) to be received within a vapor deliver device 10, and in particular, sized and shaped to fit within a heat-not-burn (HNB) vapor delivery device of the type described herein.

The foregoing is a description of various exemplary embodiments of the present invention given for purposes of explanation and illustration only. Although various embodiments of vapor delivery devices 10 and pellet substrates 31 configured for use with vapor delivery devices 10 operable to vaporize and deliver an aerosol to a user have been described herein with reference to the accompany drawing figures, other embodiments of the invention may exist or become later known that perform similar functions and/or achieve similar results. All such equivalents are considered to be within the spirit and scope of the present invention, and thus, are intended to fall within a broadest reasonable interpretation and construction of the appended claims consistent with the foregoing written description and the accompanying drawings.

That which is claimed is:

1. A dry pellet substrate for use in a vapor delivery device to vaporize and deliver an aerosol to a user, comprising:
   a semi-porous base material;
   a liquid solution comprising an aerosol former and at least one of a tobacco extract and a tobacco powder; and
   a coating comprising a water soluble gum.

2. The dry pellet substrate according to claim 1, wherein the base material is selected from the group consisting of hulled millet grains and cellulose paper.

3. The dry pellet substrate according to claim 1, wherein the base material is in the form of pellets that have a mesh size between about 4 and about 30.

4. The dry pellet substrate according to claim 1, wherein the aerosol former is selected from the group consisting of glycerin, vegetable glycerin, propylene glycol and combinations thereof.

5. The dry pellet substrate according to claim 1, wherein the coating is a mixture comprising a liquid hydrocolloid gum and distilled water, and wherein the mixture is coated onto the base material and subsequently dried.

6. The dry pellet substrate according to claim 1, wherein the water soluble gum comprises a cellulose gum.

7. The dry pellet substrate according to claim 1, wherein the coating is a mixture comprising sodium carboxymethylcellulose (NaCMC), and wherein the concentration of the sodium carboxymethylcellulose (NaCMC) in the mixture is between about 0.01% and about 5.0%.

8. The dry pellet substrate according to claim 7, wherein the concentration of the sodium carboxymethylcellulose (NaCMC) in the mixture is greater than about 0.01% and less than about 1.0%.

9. The dry pellet substrate according to claim 1, wherein the liquid solution further comprises at least one of a flavoring and nicotine.

10. A dry pellet substrate for use with a vapor delivery device to vaporize and deliver an aerosol to a user, comprising:
    a base material in the form of a semi-porous pellet having a plurality of exposed surfaces and made of at least one of activated alumina, activated carbon, hulled millet grains and cellulose paper;
    a coating comprising a water soluble gum; and
    a liquid solution comprising an aerosol former and at least one of a tobacco extract and a tobacco powder;
    wherein the base material and the liquid solution are admixed together such that the liquid solution is adsorbed onto the exposed surfaces of the pellet; and wherein at least a portion of the liquid solution is vaporized when the pellet is heated to form an aerosol to be delivered to the user.

11. The dry pellet substrate according to claim 10, wherein the base material is coated with a mixture comprising the water soluble gum and distilled water.

12. The dry pellet substrate according to claim 11, wherein the water soluble gum is selected from the group consisting of a liquid hydrocolloid gum and a cellulose gum, and wherein the concentration of the water soluble gum in the mixture is between about 0.01% and about 5.0%.

13. A method of forming a dry pellet substrate for use with a vapor delivery device comprising:

providing a semi-porous base material having a plurality of exposed surfaces and selected from the group consisting of activated alumina pellets, activated carbon pellets, hulled millet grains and cellulose paper;

providing a liquid solution comprising an aerosol former and at least one of a tobacco extract and a tobacco powder;

admixing the base material and the liquid solution together;

allowing the liquid solution to adsorb onto the plurality of exposed surfaces of the base material;

allowing the liquid solution to dry until the exposed surfaces of the base material are essentially dry; and coating the base material with a mixture comprising a water soluble gum and distilled water.

14. The method according to claim 13, wherein the mixture is a liquid hydrocolloid gum solution.

15. The method according to claim 13, wherein the water soluble gum comprises sodium carboxymethylcellulose (NaCMC).

16. The method according to claim 14, wherein the liquid hydrocolloid gum solution is dried from the plurality of exposed surfaces of the base material before the base material and the liquid solution are admixed together.

* * * * *